US011382532B1

(12) United States Patent
Hajianpour (10) Patent No.: US 11,382,532 B1
(45) Date of Patent: Jul. 12, 2022

(54) APPARATUS FOR MEASURING A HEIGHT OF A CHILD (71) Applicant: Zoya Hajianpour, Fort Lauderdale, FL (US)

(72) Inventor: Zoya Hajianpour, Fort Lauderdale, FL (US)

( * ) Notice: Subject to any disclaimer, the term of this patent is extended or adjusted under 35 U.S.C. 154(b) by 512 days.

(21) Appl. No.: 16/504,289

(22) Filed: Jul. 7, 2019

(51) Int. Cl.
*A61B 5/103* (2006.01)
*A61B 5/107* (2006.01)
*G01B 5/06* (2006.01)

(52) U.S. Cl.
CPC .......... *A61B 5/1072* (2013.01); *A61B 5/1075* (2013.01); *G01B 5/061* (2013.01)

(58) Field of Classification Search
CPC .............................. A61B 5/1072; G01B 5/061
USPC ............................................................ 33/512
See application file for complete search history.

(56) References Cited

U.S. PATENT DOCUMENTS

| | | | | |
|---|---|---|---|---|
| 1,974,085 A * | 9/1934 | Shields | .................. | G01B 5/061 33/512 |
| 1,985,527 A * | 12/1934 | Taylor | ................... | G01G 19/50 33/512 |
| 2,215,884 A * | 9/1940 | Runge | ..................... | G01B 5/02 126/30 |
| 2,381,428 A * | 8/1945 | Attick | .................. | A61B 5/1072 33/720 |
| 8,109,008 B1 * | 2/2012 | Niemczak | ............ | A61B 5/1079 600/587 |
| 8,322,043 B2 * | 12/2012 | Cha | ...................... | A61B 5/1072 33/832 |
| 8,528,221 B2 * | 9/2013 | Glock, Jr. | ............ | A61B 5/1072 600/587 |
| 8,539,690 B2 * | 9/2013 | Haykeen | .............. | A61B 5/1072 600/587 |
| 8,845,332 B1 * | 9/2014 | Reid | .................... | A61B 5/1072 702/173 |
| 8,869,415 B1 * | 10/2014 | Haykeen | .............. | A61B 5/1072 33/485 |
| 10,788,305 B1 * | 9/2020 | Neu | ..................... | G01B 3/1048 |
| 10,895,453 B2 * | 1/2021 | Stemkens | .............. | G01B 13/00 |
| 11,172,847 B2 * | 11/2021 | Johnston | ............ | G01B 11/0608 |
| 2014/0109425 A1 * | 4/2014 | Brotman | .................. | G01B 3/10 33/759 |
| 2014/0202017 A1 * | 7/2014 | Wood | ...................... | G01B 3/20 33/512 |
| 2021/0244315 A1 * | 8/2021 | Malcolm | .................. | G01C 5/00 |

* cited by examiner

*Primary Examiner* — George B Bennett
(74) *Attorney, Agent, or Firm* — Malin Haley DiMaggio & Bowen, P.A.

(57) ABSTRACT

A device for measuring a height of a child standing on a floor includes a track member attached to a wall, a mirror to keep the attention of the child during the measuring process, and a visible scale and a carriage, each attached to the track member, with the carriage being vertically movable along the track member. When a measurement surface of the carriage is held against a top of the head of the child, an indicator on the carriage points to a location on the visible scale indicating the height of the child.

17 Claims, 6 Drawing Sheets

APPARATUS FOR MEASURING A HEIGHT OF A CHILD

RELATED APPLICATIONS

Not applicable.

FEDERALLY SPONSORED RESEARCH OR DEVELOPMENT

Not applicable

BACKGROUND OF THE INVENTION

Field of the Invention

This invention relates to an apparatus and a method for measuring a height of a child, and, more particularly, to such an apparatus including a device for maintaining the attention of the child during the measurement process.

Background of the Invention

While devices for measuring the height of babies, toddlers, and adults are well known, it is additionally known that it is often difficult to keep a baby or child still enough for the measurement process to be completed with conventional measuring apparatus. It is further known that babies, being fascinated when they see themselves in a mirror, often pause when they are presented with a mirror. The method of providing a mirror in a place where people have too wait works with adults, too, and has been used by hotels providing large mirrors adjacent elevator doors to avoid the alternative expense of providing additional elevators to reduce wait times.

While many individuals note their child's growth progress with a series of markings on a wall, and while a number of colorful posters are available for receiving such markings after being attached to a wall, what is needed is an apparatus for easily determining a child's growth progress in terms of measured units, such as inches or centimeters, for comparison with various forms of standard growth data.

SUMMARY OF THE INVENTION

In accordance with an aspect of the invention, an apparatus is provided for measuring aa height of a child standing at a predetermined location. The apparatus includes a track member attached to a wall, a visible scale attached to the track member, a carriage attached to the track member to be movable along the track member only vertically, a brake member movably attached to the carriage and held in contact with the track member to stop and prevent motion of the carriage along the track member, and a mirror attached to the track member to be visible to the child standing in the preferred location, The carriage includes a downward-facing measurement surface and an indicator moving adjacently along the visible scale, pointing to a place on the visible scale describing a vertical distance between the downward-facing measurement surface and the predetermined location.

In one version of the invention, the apparatus additionally includes a frame member extending along a distal side of the mirror, with the track member extending along a proximal side of the mirror, and with the mirror being attached to extend between the track member and the frame member. This version of the apparatus additionally includes an upper end cap attached to the wall, having sockets holding upper ends of the track member and the frame member, and a lower end cap attached to the wall, having sockets holding lower ends of the track member and the frame member, so that the track member is attached to the wall by the upper and lower end caps. Furthermore, in this version of the apparatus, the track member may include a slot holding a proximal edge of the mirror, while the frame member includes a slot holding a distal edge of the mirror, while the upper end cap includes a slot holding an upper edge of the mirror, and while the lower end cap includes a slot holding a lower edge of the mirror.

In another version of the invention, the apparatus additionally includes a main plate extending in a distal direction from the track member. The main plate includes a curved proximal flange forming a slot holding a proximal edge of the mirror and a distal flange curved to form a slot holding a distal edge of the mirror. The track member is attached to the proximal flange, and the main plate is attached to the wall, so that the track member is attached to the wall by the main plate. The apparatus further includes upper and lower end caps holding the mirror to extend between the slot in the proximal flange and the slot in the distal flange by closing openings within the main plate above and below the mirror. The apparatus may additionally include a first pair of attachment screws, each extending through a clearance hole in the upper cap and through a clearance hole in an upper strip of the main plate to engage a threaded hole in a clamping block held within a slot in the main plate and to clamp the upper strip of the main plate between the clamping block and the upper cap, and a second pair of attachment screws, each extending through a clearance hole in the lower cap and through a through a clearance hole in a lower strip of the main plate to engage a threaded hole in a clamping block held within a slot in the main plate and to clamp the lower strip of the main plate between the clamping block and the lower cap.

In yet another version of the invention, the apparatus additionally comprises a mirror holding member, attached to the carriage and moving with the carriage, holding the mirror. This version of the apparatus additionally includes an upper end cap attached to the wall, having a socket holding an upper end of the track member, and a lower end cap attached to the wall, having a socket holding lower end of the track member, whereby the track member is attached to the wall by the upper and lower end cap.

For example, the brake member comprises a brake lever, pivotally mounted within the carriage, held in contact with the track member by a spring member, while the brake releasing member comprises a knob, slidably mounted within the carriage to move horizontally in and opposite a brake releasing direction, wherein movement of the knob in the brake releasing direction moves the brake lever away from the track member, and wherein movement of the knob in a vertical direction with the brake lever held away from the track member causes movement of the carriage in the vertical direction along the track member. Alternatively, the brake releasing member comprises a knob, slidably mounted within the carriage to move horizontally in and opposite a brake releasing direction, wherein movement of the knob in the brake releasing direction moves the brake lever away from the track member, and wherein movement of the knob in a vertical direction with the brake lever held away from the track member causes movement of the carriage in the vertical direction along the track member.

In accordance with another aspect of the invention, a kit is provided, including the apparatus as described above for measuring a height of a child standing in a preferred location. The kit may additionally include an assembly fixture locating the lower end cap or the main plate on a wall so that the lower end of the track member placed within the lower end cap will be spaced away from the floor surface by the predetermined distance, In accordance with yet another aspect of the invention, a method is provided for installing a first apparatus for measuring a height of a child standing in a predetermined location. The method includes attaching a lower end cap to a wall at a predetermined distance from a floor surface extending outward from the wall, installing a second apparatus including a track member, a visible scale attached to the track member, a mirror facing the predetermined location, and a carriage attached to the track member to be movable along the track member only vertically, including a downward-facing measurement surface and an indicator moving adjacently along the visible scale, wherein the indicator points to a place on the visible scale describing a vertical distance between the downward-facing measurement surface and the floor surface to extend upward along the wall from a socket within the lower end cap; and attaching an upper end cap to the wall to hold an upper end an upper end of the second apparatus. The second additionally comprises a frame member extending along a distal side of the mirror, wherein the track member extends along a proximal side of the mirror, and wherein the mirror is attached to extend between the track member and the frame member, or alternately the second apparatus may include a mirror holding member, attached to the carriage and moving with the carriage, holding the mirror.

BRIEF DESCRIPTION OF THE DRAWINGS

These and other aspects of the invention will be made apparent by reading the following specification in conjunction with the accompanying figures, in which.

DETAILED DESCRIPTION OF THE INVENTION

An apparatus 100 built in accordance with a first embodiment of the invention for measuring a height of a child will first be discussed with reference being made to FIG. 1, a front elevation of the apparatus 100, which includes a track member 102, a frame member 104, disposed laterally from the track member 102 in the direction of arrow 106 to hold a mirror 108, an upper cap 108, a lower cap 110, and a carriage 112, movable upward, in the direction of arrow 114, and downward, opposite the direction of arrow 114, along the track member 102. The track member 102 includes a visible scale 116, while the carriage 112 includes an indicator 118 pointing to a location on the visible scale 116 describing a distance 120 between a surface 122 of a floor 124 extending outward from a wall 126 to which the apparatus 100 is attached and a measurement surface 128 of the carriage 112, and with the distance 120 being described, for example, in inches or centimeters. Preferably, the apparatus 100 is fastened to the wall 126 by a number of screws 130 extending through slots (not shown) in the upper cap 108 and the lower cap 110.

Figure 2:
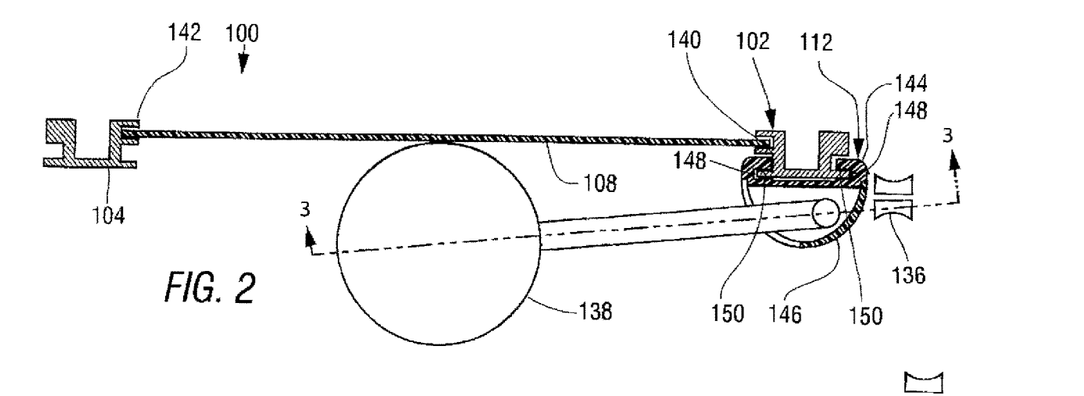
FIG. 2 is a fragmentary cross-sectional plan view of the apparatus of FIG. 1, taken as indicated by section line 2-2 therein.

FIG. 2 is a fragmentary cross-sectional plan view of the apparatus 100, taken as indicated by section line 2-2 in FIG. 1, showing the mirror 108 as being held to extend between a first slot 140 in the track member 102 and a second slot 142 in the frame member 104. The carriage 112 is shown as including a housing 144 and a cover 146. The housing 144 slides upward and downward on the track member 102, with a guiding rib 148 extending outward from each side of the track member 102 sliding within a guiding slot 150 of the housing 144.

Figure 3:
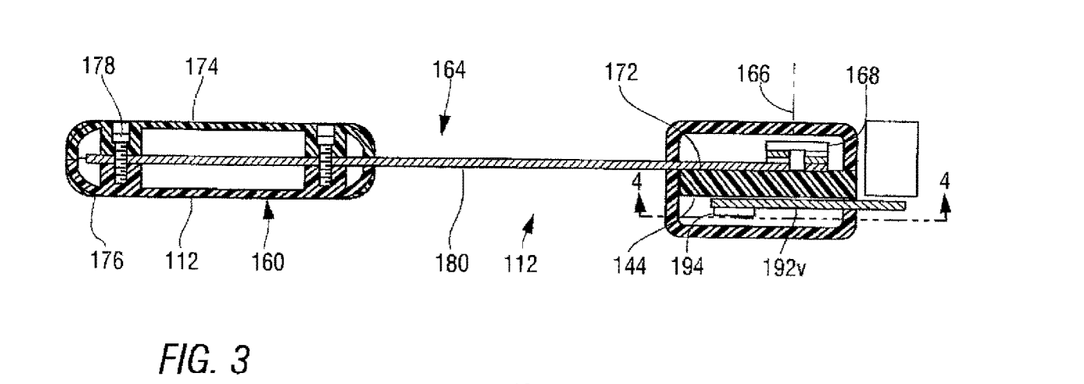
FIG. 3 is a fragmentary cross-sectional oblique elevation of the apparatus of FIG. 1, taken as indicated by section line 3-3 in FIG. 2.

FIG. 3 is a fragmentary cross-sectional oblique elevation of the apparatus 100, taken as indicated by section line 3-3 in FIG. 2, showing the measurement surface 128 of the carriage 112 as being formed along a lowest surface of a measurement structure 160 at an end 162 of a measurement arm 164, which is attached to pivot about a vertical axis 166 of the housing 144. For example, the vertical axis 166 is established by a pivot screw 168 fastened to the housing 144, with a wave washer 170 holding the measurement arm 164 against an upwardly facing surface 172 of the housing 144, while the measurement structure 160 is formed by clamping an upper section 174 to a lower section 176, with a bar 180 extending through a slot 182 within the cover 146 from the pivot screw 168 being clamped between the sections 174, 176.

Figure 4:
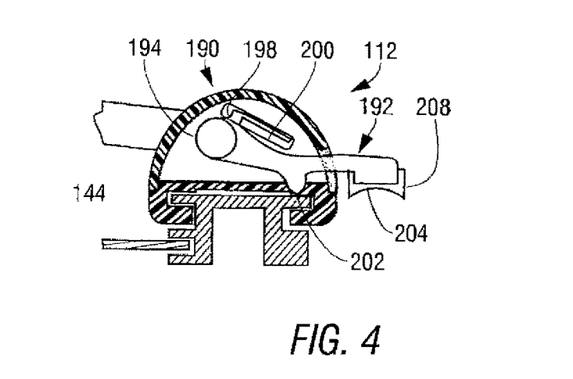
FIG. 4 is a fragmentary cross-sectional underneath plan view of the apparatus of FIG. 1, taken as indicated by section line 4-4 in FIG. 3.

FIG. 4 is a fragmentary cross-sectional underneath plan view of the apparatus 100, taken as indicated by section line 4-4 in FIG. 3, showing a braking mechanism 190 that is provided for holding the carriage 112 in place on the track member 102. The braking mechanism 190 includes a brake lever 192, which is pivotably attached to the housing 144 by a pivot screw 194. The brake lever 192 includes a spring member 196, which extends upward into a cavity 198 within the housing 144, contacting a surface 200 of the cavity 198 to provide a force holding a braking surface 202 against the track member 102. The brake lever 192 further includes a tab 204, extending within a release pad 208 to attach the release pad 208 to the brake lever 192, which is then released from contact with the track member 102 by movement of the release pad 208 in the forward direction of arrow 210. The housing 144 preferably includes a guiding pad 212 disposed adjacent to, but spaced away from, the release pad 208, so that these pads 208. 212 can be squeezed together, using outward-facing, concave surfaces 214 thereof, to release the braking mechanism 190 and to move the carriage 112 as desired.

Figure 1:
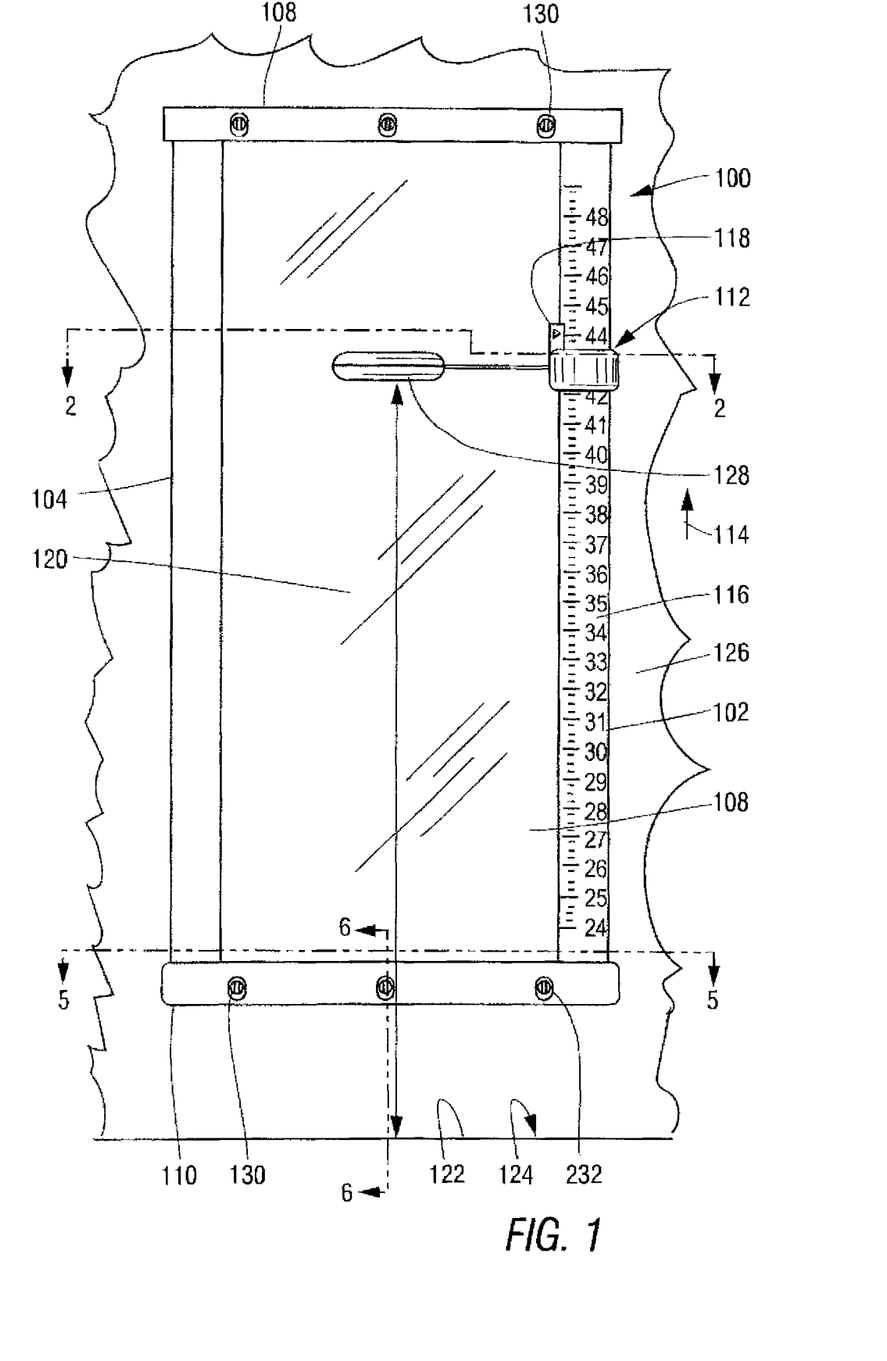
FIG. 1 is a front elevation of apparatus for measuring a height of a child, built in accordance with a first embodiment of the invention.
Figure 5:
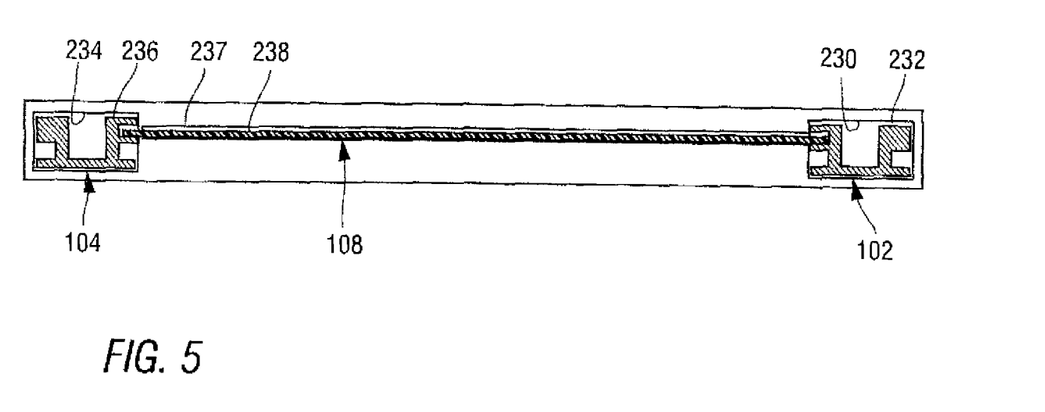
FIG. 5 is a cross-sectional plan view of the apparatus of FIG. 1, taken as indicated by section line 5-5 therein.

FIG. 5 is a cross-sectional plan view of the apparatus 100, taken as indicated by section line 5-5 in FIG. 1, showing that a lower cap 110 therein includes a first socket 230, holding a lower end 232 of the track member 102, a second socket 233, holding a lower end 234 of the frame member 104, and a central slot 236, holding a lower edge portion 238 of the mirror 108. As shown in FIG. 1, the upper cap 108 is preferably identical to the lower cap 110, with the upper cap 108 being installed in an inverted orientation to hold an upper end 240 of the track member 102, an upper end 242 of the frame member 104, and an upper edge portion 246 of the mirror 108. Both the upper cap 108 and the lower cap 110 include a number of outwardly-open sockets 238, through which screws 130 extend to attach the caps 108, 110 to the wall 126.

Figure 6:
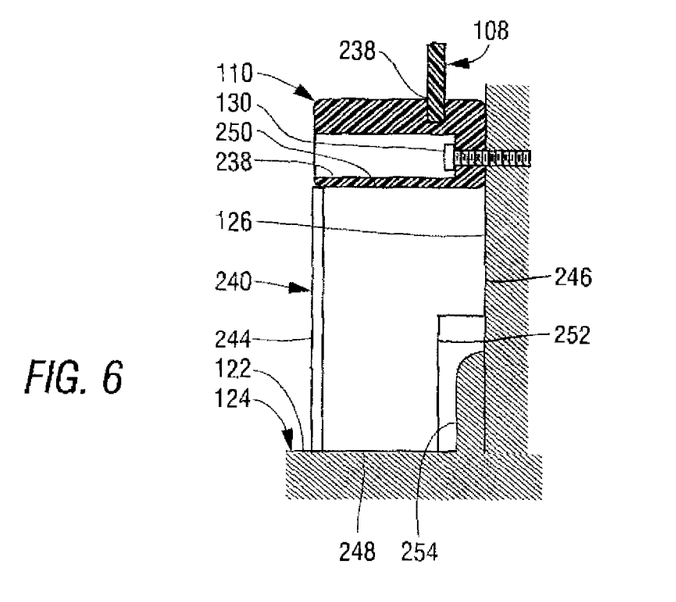
FIG. 6 is a right elevation of a lower cap within the apparatus of FIG. 1, shown as installed using an assembly fixture.

FIG. 6 is a right elevation of the lower cap 110, shown as installed on the wall 126 in first step of a preferred process for assembling and installing the apparatus 100, with this first step attaching lower cap 110 to the wall 126 with a number of screws 130 as the lower end cap 110 is held atop an assembly fixture 240, which is preferably provided with the apparatus 100 so that, during subsequent use of the apparatus 100, conditions described above in reference to FIGS. 1 and 3 will be met, with the distance 120 between the measurement surface 128 of the carriage 112 and a surface 122 8f the floor 124 being indicated by the location of the indicator 110 on the visible scale 116 as the carriage 112 is moved upward and downward along the track member 102. For example, the assembly fixture 240 includes a pair of identical side plates 242 extending at each end of a connecting plate 244, with each of the side plates 242 including a first surface 246 configured to rest against the wall 126, a second surface 248 configured to rest against the surface 122 of the floor 124, and a third surface 250, configured to support the lower cap 110. A fourth surface 252 is recessed to avoid contact with a molding 254, which may be present.

After the first step of the assembly and installation process is completed, as described above in reference to FIG. 6, the lower end 232 of the track member 102 and the lower end 234 of the frame member 104 are inserted into the sockets 230, 233, and the lower edge portion 238 of the mirror is inserted into central slot 236, so that the track member 102, the frame member 104, and the mirror 108 extend upward from the lower cap 110. The carriage 112 may have been previously installed to slide along the track member 102, or it may be instead installed on the track member 102 at this time. In either case, the upper cap 108 is then attached to the wall 126 as shown n FIG. 1 to hold upper end portions of the track member 102, the frame member 104, and the mirror 108.

Figure 7:
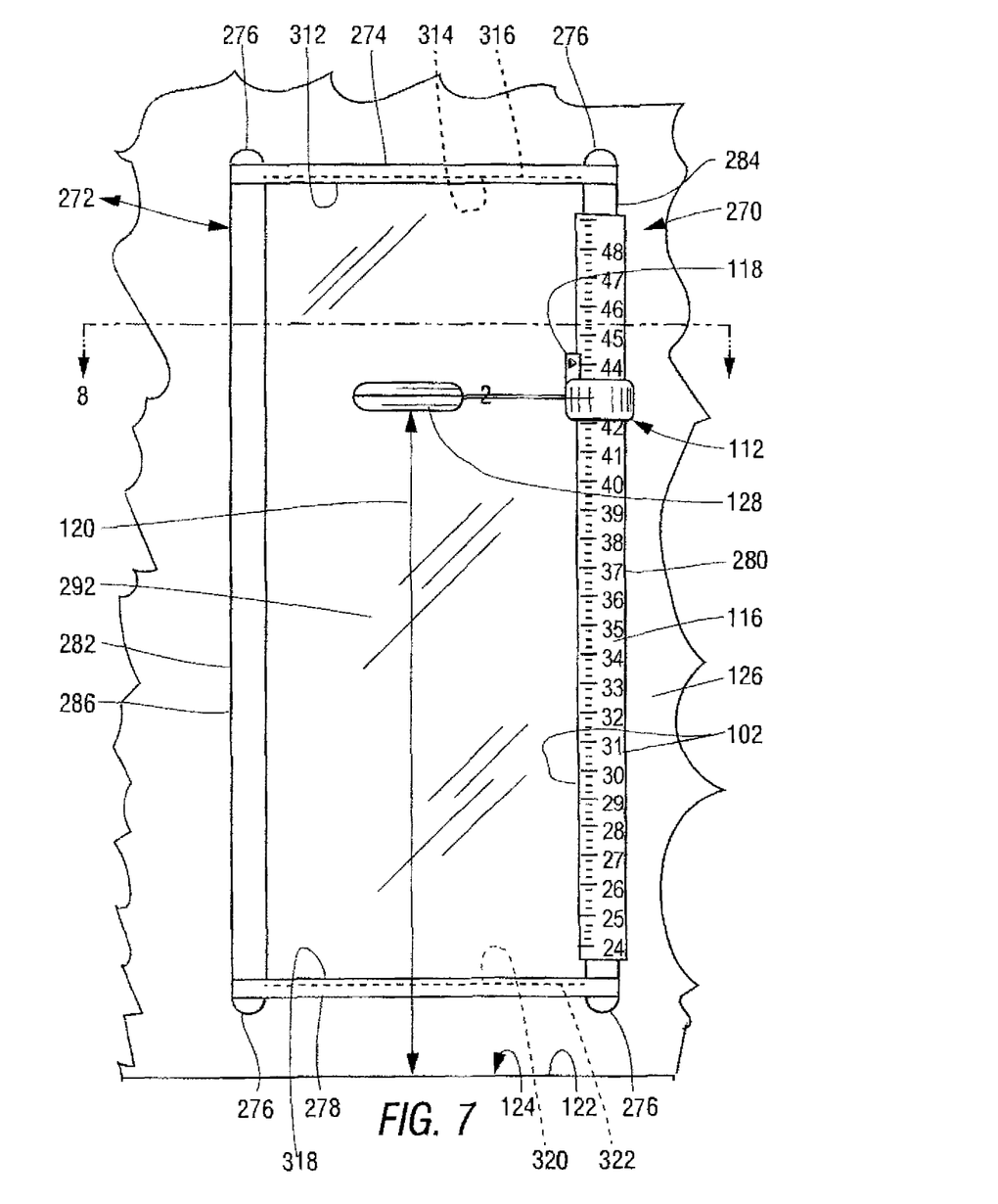
FIG. 7 is a front elevation of an apparatus for measuring a height of a child, built in accordance with a second embodiment of the invention.
Figure 8:
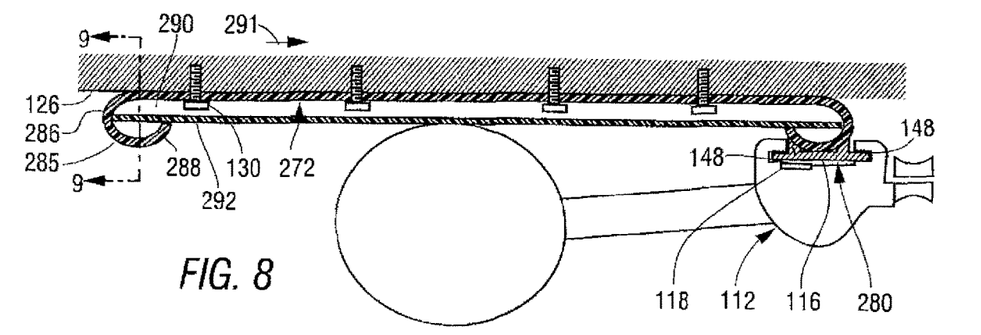
FIG. 8 is a cross-sectional plan view of the apparatus of FIG. 7, taken as indicated by section line 8-8 therein.
Figure 9:
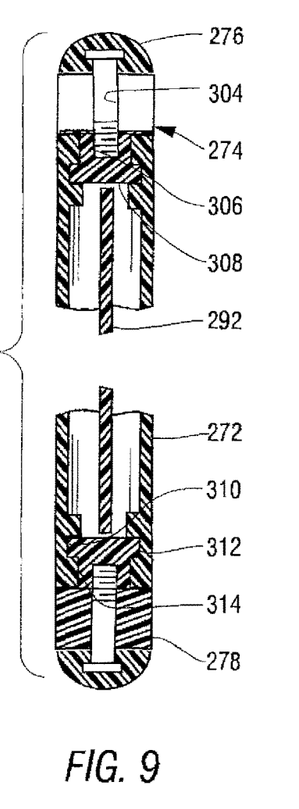
FIG. 9 is a fragmentary cross-sectional elevation of the apparatus of FIG. 7, taken as indicated by section line 9-9 in FIG. 8.

An apparatus 270 built in accordance with a second embodiment of the invention will now be discussed, with reference being made to FIGS. 7-9. FIG. 7 is a front elevation of the apparatus 270, while FIG. 8 is a cross-sectional plan view thereof, taken as indicated by section line 8-8 in FIG. 7, and while FIG. 9 is a fragmentary cross-sectional elevation thereof, taken as indicated by section line 9-9 in FIG. 8. With elements similar or identical to the elements described above in reference to the apparatus 100 being accorded like reference numerals, it is noted that the apparatus 270 includes a main plate 272, which is attached to wall 126 by a number of screws 130, an upper end cap 274, attached to the main plate 272 by two attachment screws 276, a lower end cap 278, also attached to the main plate 272 by two attachment screws 276, a track member 280, adhesively attached to the main plate 272, a visible scale 116, extending along the track member 280, and a carriage 112, engaging the outstanding ribs 148 of the track member 280 as described above regarding the first apparatus 100 so that the carriage 112 can be moved upward and downward along the track member 280 and held at a desired location, with an indicator 118 on the carriage 112 pointing to a location on the visible scale 116 describing a distance 120 between a measurement surface 128 on the carriage 112 and a surface 122 of a floor 124 extending outward from the wall 126, again as described above regarding the apparatus 100. The main plate 272 includes a curved edge section 282 extending along a right edge 284 and a left edge 285, with each of the curved sections including a outwardly curved section 286 and an inwardly curved section 288, and an open slot 290, facing in the inward direction of arrow 291 to hold a mirror 292 extending between the two curved edge sections 282.

Since the apparatus 270 is configured so that the screws 130 attaching the main plate 270 to the wall 120 are hidden by the mirror 292, the main plate 270 must be attached to the wall 120 before the mirror 292 is installed within the main plate 272. Preferably, such an attachment to the wall is done using an assembly fixture to establish a desired distance between the surface 122 of the floor 124 and a feature of the main plate 272, in the manner generally described above in reference to FIG. 6. Then, the lower end cap 278 is attached to the main plate 272 by two attachment screws 276, closing an opening at a lower end 294 of the main plate 272. Next, the mirror 292 is inserted into an opening at the upper end 296 of the main plate 272 and lowered until a lower end 298 of the mirror 292 extends into a slot 300 within the lower end cap 278. Then, the upper end cap 274 is installed to extend along the upper edge 302

As shown in FIGS. 7 and 9, the upper end cap 274 is attached to the main plate 272 by two attachment screws 276, each extending through a clearance hole 304 within the upper end cap 274 to engage a threaded hole 306 within an attachment block 308, disposed in an attachment slot 310, which is open to the adjacent left side 282 or right side 284 so that the attachment block can be inserted into the attachment slot 310. The attachment block 308 includes a distal flange 312 engaging a proximal flange 314 within the attachment slot 310. Similarly, the lower end cap 278 is attached to the main plate 272 by two attachment screws 276, each extending through a clearance hole 304 within the upper end cap 274 to engage a threaded hole 306 within an attachment block 308, disposed in an attachment slot 310, which is open to the adjacent left side 282 or right side 284 so that the attachment block can be inserted into the attachment slot 310. Again, the attachment block 308 includes a distal flange 312 engaging a proximal flange 314 within the attachment slot 310. As shown in FIG. 7, for example, a lower surface 312 of the upper end cap 274 includes a slot 314 for receiving an upper edge 316 of the of the mirror 292, while n upper surface 318 of the lower end cap 278 include a slot 320 for engaging a lower end 322 of the mirror 292.

Figure 10:
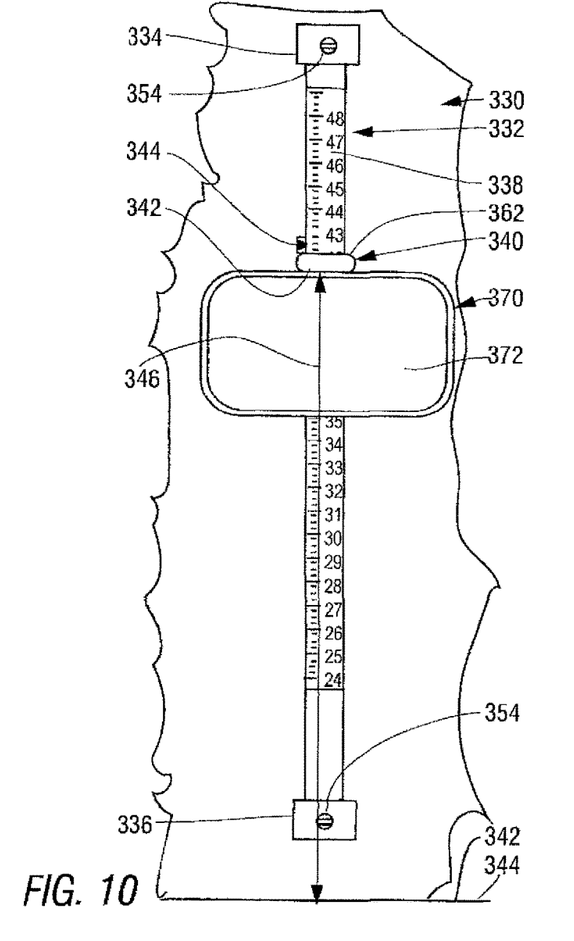
FIG. 10 is a front elevation of an apparatus for measuring a height of a child, built in accordance with a third embodiment of the invention.
Figure 11:
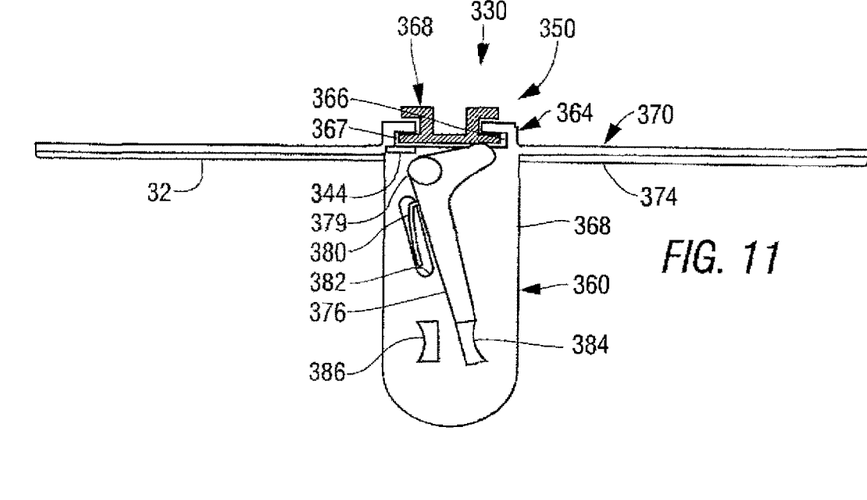
FIG. 11 is a cross-sectional plan view of the apparatus of FIG. 10, taken as indicated by section line 11-11 therein.

An apparatus 330 built in accordance with a third embodiment of invention will now be discussed, with reference being made to FIGS. 10 and 11. FIG. 10 is a front elevation of the apparatus 330, while FIG. 11 is a cross-sectional plan view thereof, taken as indicted by section lines 11-11 in FIG. 10. The apparatus 330 includes a track member 332, extending between an upper end cap 334 and a lower end cap 336, a visible scale 338 attached to the track member 332, and a carriage 340 movable upward and downward along the track member 332, The carriage 340 includes a measurement surface 342 extending along its lowest surface thereof and an indicator 344 pointing to a location on the visible scale 338 describing the distance 346 between the measurement surface 340 and a surface 342 of a floor 344 extending outward from a wall 350 to which 350 to which the apparatus 352 is attached by screws 354 extending through the end caps 334, 336. Preferably, the lower end cap 336 is installed first, being spaced way from the floor 350 by the method described above in reference to FIG. 6, through the use of an assembly fixture.

The carriage 350 further includes a housing 360 and a cover 362, which is snapped into place over the housing 360. (In FIG. 11, the housing 360 is shown with the cover 362 removed to reveal internal elements.) The housing 360 incudes a track engaging portion 364 having a pair of slots 366 sliding on a pair of ribs 367 within the track member 332, a forward extending portion 368 providing controls for moving and stopping movement of the carriage 350, and a downward extending portion 370 holding a mirror 372, which is held in place on the housing 360 by a snap-on mirror frame 374. For example, a brake lever 376 is provided for engaging a surface 378 of the track member 332 to prevent movement of the carriage 350 along the track member 332. The brake lever 376 is pivotally mounted on the forward extending portion 368 of the housing 360 by a pivot screw 379, with a spring portion 380 of the brake lever 376 engaging a cavity 382 within the forward extending portion 368 to provide a force engaging the track member 332. This force is overcome, allowing movement of the carriage 350 along the track member 332 by pushing a concave surface 384 attached to the brake lever 376. The carriage 350 is then moved into a desired position by holding the concave surface 384 and a contact surface 386 squeezed together.

Figure 12:
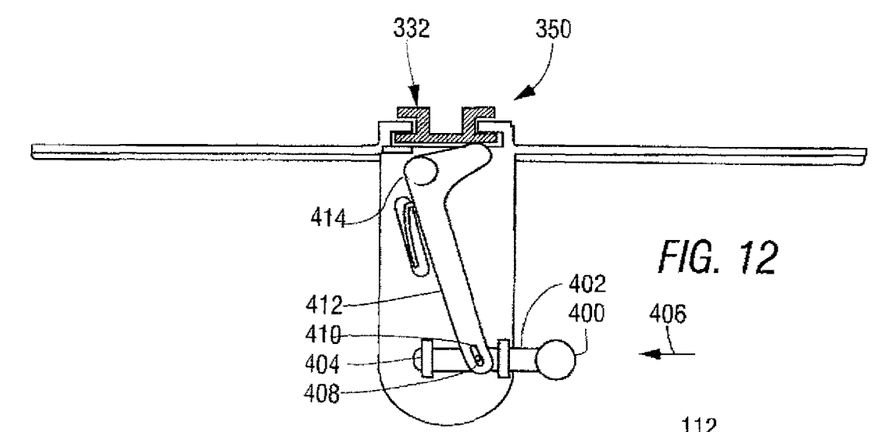
FIG. 12 is a plan view of a carriage within the apparatus of FIG. 10, shown as configured in accordance with an alternative embodiment of the invention.
Figure 13:
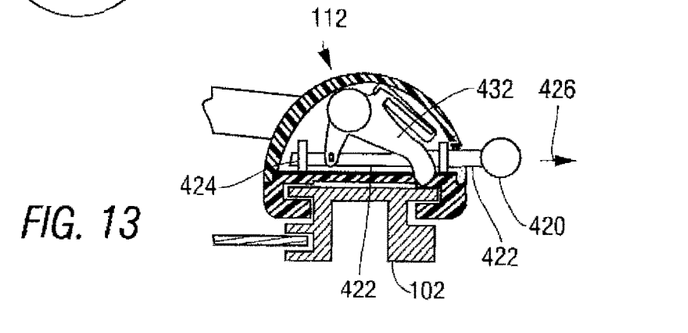
FIG. 13 is a plan view of a carriage within the apparatus of FIG. 1 or of FIG. 7, shown as configured in accordance with the alternative embodiment of the invention.

An alternative embodiment for releasing and moving the carriage 350, 112 will now be discussed, with reference being made to FIGS. 12 and 13. FIG. 12 is a plan view of the carriage 350 as configured in accordance with the alternative embodiment, shown with a cover 362 removed therefrom to reveal internal elements, while FIG. 13 is a fragmentary cross-sectional underneath plan view of the carriage 112, within either the apparatus 100 or the apparatus 270, with the cross-sectional view being taken as indicated by section lines 4-4 in FIG. 3, and wherein the carriage 112 is configured in accordance with the alternative embodiment. As shown in FIG. 12, when an external knob 400, attached to a non-circular shaft 402, slidably mounted in non-circular holes 404, is pushed in the direction of arrow 406, a pin 408, attached to the non-circular shaft 402 to extend through a slot 410 in a brake lever 412, causes the brake lever 412 to rotate about a pivot screw 414, being pulled away from the track member 332. As the brake lever 412 is then held away from the track member 332, the carriage 350 can be moved upward and downward, with the spring member 415 again holding the brake lever 412 against the track member 332 after the external knob 400 is released. Similarly, as shown in FIG. 13, when an external knob 420, attached to a non-circular shaft 422, slidably mounted in non-circular holes 424, is pulled in the direction of arrow 426, a pin 428, attached to the non-circular shaft 422 to extend through a slot 430 in a brake lever 432, causes the brake lever 432 to rotate about a pivot screw 434, being pulled way from the track member 102. As the brake lever 432 is then held away from the track member 102, the carriage 112 can be moved upward and downward, with the spring member 435 again holding the brake lever 432 against the track member 102 after the external knob 400 is released.

It is noted that the various versions and embodiments described above may be provided in kit form for installation in a house or other building.

While the invention has been described in terms of a number of embodiments with some degree of particularity, it is understood that these descriptions are given only by way of example, and that many variations, including the combination of elements of the various embodiments, may be made without departing from the spirit and scope of the invention, as defined within the appended claims.

What is claimed is:

1. An apparatus for measuring a height of a child standing at a predetermined location, wherein the apparatus comprises:
   a track member attached to a wall;
   a visible scale attached to the track member;
   a carriage attached to the track member to be movable along the track member only vertically, including a downward-facing measurement surface and an indicator moving adjacently along the visible scale, wherein the indicator points to a place on the visible scale describing a vertical distance between the downward-facing measurement surface and the predetermined location;
   a brake member movably attached to the carriage and held in contact with the track member to stop and prevent motion of the carriage along the track rail;
   a brake releasing member movably attached to the carriage to be moved to move the brake member away from the track rail; and
   a mirror attached to the track member to be visible to the child standing in the preferred location.

2. The apparatus of claim 1, additionally comprising:
   a frame member extending along a distal side of the mirror, wherein the track member extends along a proximal side of the mirror, and wherein the mirror is attached to extend between the track member and the frame member;
   an upper end cap attached to the wall, having sockets holding upper ends of the track member and the frame member; and
   a lower end cap attached to the wall, having sockets holding lower ends of the track member and the frame member, whereby the track member is attached to the wall by the upper and lower end caps.

3. The apparatus of claim 2, wherein
   the track member includes a slot holding a proximal edge of the mirror,
   the frame member includes a slot holding a distal edge of the mirror,
   the upper end cap includes a slot holding an upper edge of the mirror, and
   the lower end cap includes a slot holding a lower edge of the mirror.

4. The apparatus of claim 1, additionally including:
   a main plate extending in a distal direction from the track member, including a curved proximal flange curved to form a slot holding a proximal edge of the mirror and a distal flange curved to form a slot holding a distal edge of the mirror, wherein the track member is attached to the proximal flange, wherein the main plate is attached to the wall, and whereby the track member is attached to the wall by the main plate; and upper and lower end caps holding the mirror to extend between the slot in the proximal flange and the slot in the distal flange by closing openings within the main plate above and below the mirror.

5. The apparatus of claim 4, additionally comprising:

a first pair of attachment screws, each extending through a clearance hole in the upper cap and through a clearance hole in an upper strip of the main plate to engage a threaded hole in a clamping block held within a slot in the main plate and to clamp the upper strip of the main plate between the clamping block and the upper cap; and a second pair of attachment screws, each extending through a clearance hole in the lower cap and through a through a clearance hole in a lower strip of the main plate to engage a threaded hole in a clamping block held within a slot in the main plate and to clamp the lower strip of the main plate between the clamping block and the lower cap.

6. The apparatus of claim 1, additionally comprising a mirror holding member, attached to the carriage and moving with the carriage, holding the mirror.

7. The apparatus of claim 6, additionally comprising:

an upper end cap attached to the wall, having a socket holding an upper end of the track member; and a lower end cap attached to the wall, having a socket holding lower end of the track member, whereby the track member is attached to the wall by the upper and lower end cap.

8. The apparatus of claim 1, wherein the brake member comprises a brake lever, pivotally mounted within the carriage, held in contact with the track member by a spring member, the brake releasing member comprises a first handle extending outward from the brake lever, and movable to move the brake lever away from the track member, and the carriage additionally comprises a second handle, movable with the carriage.

9. The apparatus of claim 1, wherein the brake member comprises a brake lever, pivotally mounted within the carriage, held in contact with the track member by a spring member, the brake releasing member comprises a knob, slidably mounted within the carriage to move horizontally in and opposite a brake releasing direction, wherein movement of the knob in the brake releasing direction moves the brake lever away from the track member, and wherein movement of the knob in a vertical direction with the brake lever held away from the track member causes movement of the carriage in the vertical direction along the track member.

10. A kit including an apparatus for measuring a height of a child standing at a predetermined location, wherein the kit comprises:

a track member including a lower end and an upper end;

a visible scale attached to the track member;

a carriage attached to the track member to be movable along the track member only in and opposite a first direction, including a measurement surface facing in the first direction and an indicator moving adjacently along the visible scale, wherein the indicator points to a place on the visible scale describing a distance in the first direction between the measurement surface and a location spaced apart in the first direction from the lower end of the track member by a predetermined distance;

a brake member movably attached to the carriage and held in contact with the track member to stop and prevent motion of the carriage along the track member in the first direction;

a brake releasing member movably attached to the carriage to be moved to move the brake member away from the track member; and a mirror attachable to the track member to face a direction perpendicular to the first direction.

11. The kit of claim 10, additionally of an upper end cap attachable to the wall, having a socket holding an upper end of the track member; and a lower end cap attachable to the wall, having a socket holding a lower end of the track member.

12. The kit of claim 11, additionally comprising an assembly fixture locating the lower end cap on a wall so that the lower end of the track member placed within the lower end cap will be spaced away from the floor surface by the predetermined distance.

13. The kit of claim 10, additionally comprising a main plate, attachable to the wall, holding the track member, wherein the mirror is attachable within the main plate.

14. The kit of claim 13, additionally comprising an assembly fixture locating a lower end of the main plate on a wall so that the lower end of the track member placed within the lower end cap will be spaced away from the floor surface by the predetermined distance.

15. A method for installing a first apparatus for measuring a height of a child standing at a predetermined location, wherein the method comprises:

attaching a lower end cap to a wall at a predetermined distance above a floor surface extending outward from the wall;

installing a second apparatus comprising a track member, a visible scale attached to the track member, a mirror facing the predetermined location, and a carriage attached to the track member to be movable along the track member only vertically, including a downward-facing measurement surface and an indicator moving adjacently along the visible scale, wherein the indicator points to a place on the visible scale describing a vertical distance between the downward-facing measurement surface and the floor surface to extend upward along the wall from a socket within the lower end cap; and attaching an upper end cap to the wall to hold an upper end an upper end of the second apparatus.

16. The method of claim 15, wherein the second apparatus additionally comprises a frame member extending along a distal side of the mirror, wherein the track member extends along a proximal side of the mirror, and wherein the mirror is attached to extend between the track member and the frame member.

17. The apparatus of claim 16, additionally comprising a mirror holding member, attached to the carriage and moving with the carriage, holding the mirror.

* * * * *